United States Patent [19]

Petrik

[11] Patent Number: 4,941,878
[45] Date of Patent: Jul. 17, 1990

[54] OSTOMY POUCH FLUSHER

[76] Inventor: Albert V. Petrik, One Limekiln Pke., Glenside, Pa. 19038

[21] Appl. No.: 262,382

[22] Filed: Oct. 25, 1988

[51] Int. Cl.⁵ ............................................. A61M 29/00
[52] U.S. Cl. ..................................... 604/105; 604/334
[58] Field of Search ............... 604/105, 150, 181, 183, 604/277, 332–345, 266, 268; 239/114, 115, 116; 15/104.12, 104.09, 104.1 R, 104.16, 104.31, 104.05

[56] References Cited

U.S. PATENT DOCUMENTS 827,193 7/1906 Thrash .................................. 604/105
2,223,566 12/1940 Koch ..................................... 604/334

Primary Examiner—Stephen C. Pellegrino
Assistant Examiner—Michael Rafa
Attorney, Agent, or Firm—Panitch, Schwarze, Jacobs & Nadel

[57] ABSTRACT

An ostomy pouch flusher comprising an elongate wand having fluid inlet and discharge elements adjacent to opposite ends, a handle on the wand adjacent to the inlet end, and a framework of generally parallel rods extending along and spaced from each other and the wand, to define therewith an open space for passsage of a supply fluid and ostomy waste.

5 Claims, 1 Drawing Sheet

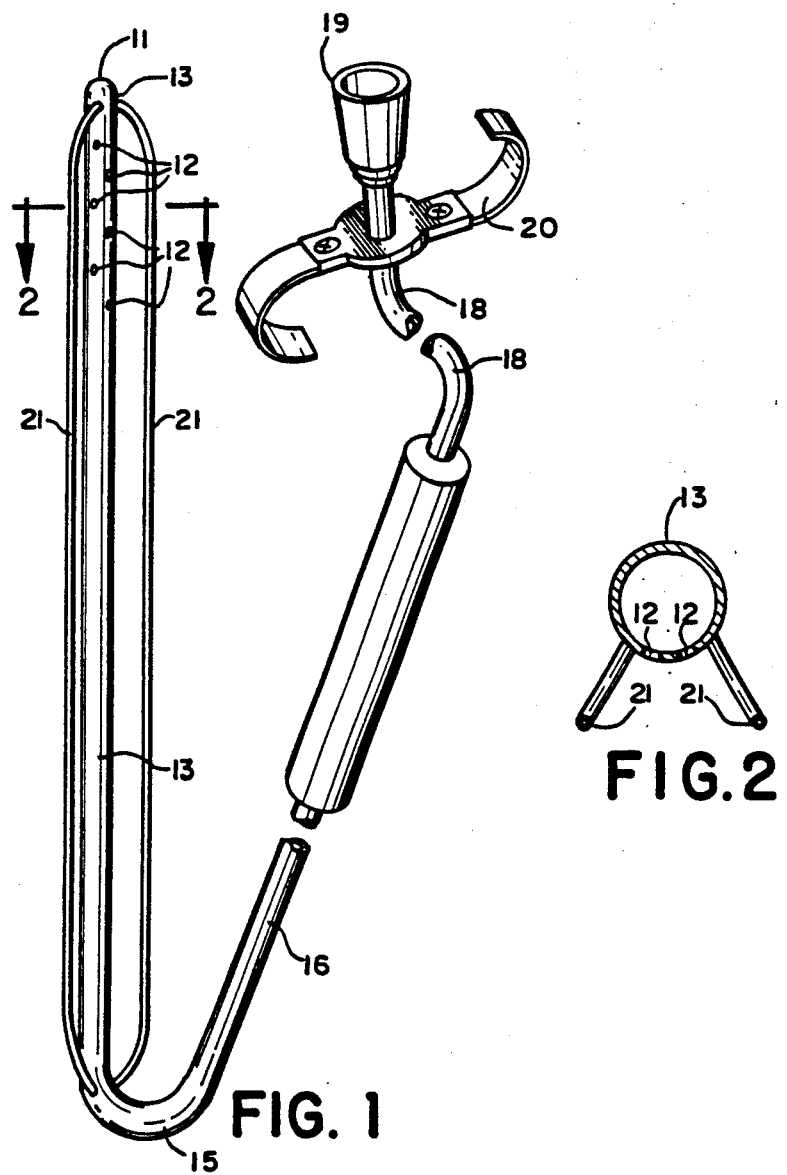

OSTOMY POUCH FLUSHER

BACKGROUND OF THE INVENTION

As is well known, certain physical conditions require a colostomy, ileostomy, and the like, wherein a pouch is connected to the person of the user for receiving body material. These conditions are generally called ostomies and the waste collection containers are called ostomy pouches.

Heretofore, the collection of body waste in an ostomy pouch, and sanitary removal of the body waste from the pouch was a difficult and time consuming procedure, at best, not always achieved with a high degree of cleanliness.

SUMMARY OF THE INVENTION

Accordingly, it is an important object of the present invention to provide an ostomy pouch flusher which overcomes the above mentioned difficulties, is insertible into an ostomy pouch to form therein an open passageway allowing flushed contents to leave the pouch without collapse of the latter.

It is a further object of the present invention to provide an ostomy pouch flusher having the advantageous characteristics mentioned in the preceding paragraph, which is smooth for scraping action without danger of tearing the pouch.

It is a further object of the present invention to provide a pouch flusher wherein water jets and frames are located in positions to prevent contact or injury to the stoma. The pouch contents are stirred and diluted in a way that complete disposal into a sink drain is possible, and the time required to clean and flush an ostomy pouch is very greatly reduced.

Other objects of the present invention will become apparent upon reading the following specification and referring to the accompanying drawings, which form a material part of this disclosure.

The invention accordingly consists in the features of construction, combinations of elements, and arrangements of parts, which will be exemplified in the construction hereinafter described, and of which the scope will be indicated by the appended claims.

BRIEF DESCRIPTION OF THE DRAWINGS

FIG. 1 is an exploded perspective view showing the ostomy pouch flusher of the present invention apart from a pouch.

FIG. 2 is a cross sectional view taken generally on the line 2—2 of FIG. 1.

DESCRIPTION OF THE PREFERRED EMBODIMENT

Referring now more particularly to the drawings, and specifically to FIG. 1 thereof, a wand is generally designated 10, and includes a generally straight, elongate member or tube 10. The tube is provided at one end, the upper end 11, as seen in the drawings, with a smoothly roundedclosure or cap 11. Adjacent to the closed end of tube 10 are a plurality of perforations or discharge openings 12.

Remote from the closed tube end 11, the tube may be reversly bent, as at 15 to extend, as at 16, generally oblique to the wand 10.

In practice, the tube 10, 15, 16 may advantageously be fabricated of stainless steel for cleanliness and a long lasting useful life. The stainless steel tubing, as at 16, may be covered with a tubular body or sheath of suitable material, as at 17, which may define a handle or handhold.

The handle 17 is connected at one end to the steel tubing part 16, and connected at its other end, as by a hose 18, to a faucet adapter 19 for connection to a supply of cold water. The faucet adapter or connecter 19 may be provided, adjacent thereto, with a holding strap 20, to facilitate connection to a faucet, or other source of fluid supply.

In addition to the stainless wand or tube 10, which may be generally straight, as shown, and about twelve inches long, the wand further includes a pair of wire frames or rods 21.

The wire rods or frames are preferably also fabricated of stainless steel, and extend in general parallelism with each other and the tube 13 to define the wand 10. Further, the rods or frame members 21 extend generally between opposite ends of the tube 13, opposite ends of the rods being smoothly arcuately bent inwardly toward and suitably affixed, as by welding, to the tube 13. That is, the rods or frames 21 are located in angularly spaced relation, say approximately 40°-60° angularly about the tube or stem 13, as best seen in FIG. 2. It will also be seen that the perforations or fluid discharge holes 12 may be angularly spaced apart from each other within the arc of the rods or frames 21.

In the use, cold water or other suitable flushing fluid is passed downwardly through handle 17 and extension 16, that reverses upwardly through tube or stem 13. The stem 13 and rods 21 combine to define an open framework, and when inserted upwardly into an ostomy pouch, the flushing fluid may pass freely through the longitudinal space defined by the framework of stem 13 and rods 21. The framework is manipulable in the ostomy pouch for flushing and scraping. The flushing and scraping may be done simultaneously with discharge of fluid from the lower end of the ostomy pouch, or may be done alternately with the flushing and scraping.

From the forgoing it is seen that the device of the present invention provides a flusher and cleaner for ostomy pouches which is extremely simple in construction, capable of quick, easy and efficient flushing, and otherwise fully accomplishes its intended objects.

Although the present invention has been described in some detail by way of illustration and example for purposes of clarity of understanding, it is understood that certain changes and modifications may be made within the spirit of the invention.

What is claimed is:

1. An ostomy pouch flusher for emptying and cleaning an ostomy pouch installed upon a user, the ostomy pouch having a first opening surrounding a stoma of the user and a second closable drain opening distal from the first opening, the flusher comprising an elongate wand comprising a hollow tube, water inlet and discharge means adjacent to opposite ends of said wand, a handle connected to said wand adjacent to said water inlet means, said tube including a reversely bent tube extension on said inlet end defining said handle, and a frame extending along at least a portion of said wand adjacent to said discharge means, said frame extending longitudinally along and spaced from a portion of said wand to define an open space, said discharge means being positioned for the discharge of flushing water only in the direction of the open space defined by the frame whereby said wand and frame are insertable into the drain opening of an ostomy pouch and movable therein to spray the interior of said pouch, said frame and said wand maintaining the ostomy pouch in an open condition to facilitate the removal of material from the ostomy pouch through the space defined by the frame and the wand, the frame, the wand and the handle cooperating to prevent movement of the flusher to a position in which the flushing water is discharged directly toward or onto the stoma.

2. An ostomy pouch flusher according to claim 1, in combination with a fluid conduit extending from said tube extension for connection to a supply of water.

3. An ostomy pouch flusher according to claim 1, wherein said frame comprises a pair of rods generally parallel to each other and having arcuate portions at opposite ends connected to said tube.

4. An ostomy pouch flusher according to claim 3, wherein said wand is comprised of a tube having one end proximate the discharge means closed and generally smooth.

5. An ostomy pouch flusher according to claim 4, in combination with a faucet adapter on said other end of said tube, for connection to a water supply.

* * * * *